United States Patent [19]

Herzig et al.

[11] Patent Number: 4,734,509

[45] Date of Patent: Mar. 29, 1988

[54] PREPARATION OF 4(5)-HYDROXYMETHYL-5(4)-METHYLIMIDAZOLE

[75] Inventors: Jacob Herzig, Raanana; Ben Z. Weiner, Jerusalem; Stephan Cherkez, Ramat Gan; Abraham Antebi, Bat-Yam, all of Israel

[73] Assignee: Teva Pharmaceutical Industries Ltd., Israel

[21] Appl. No.: 854,537

[22] Filed: Apr. 22, 1986

[30] Foreign Application Priority Data

May 1, 1985 [IL] Israel ............................................ 75063

[51] Int. Cl.$^4$ ........................................... C07D 233/64
[52] U.S. Cl. ................................................... 548/342
[58] Field of Search ........................................ 548/342

[56] References Cited

U.S. PATENT DOCUMENTS 4,275,216  6/1981  Hubert-Brierre ................... 548/342

OTHER PUBLICATIONS

J. Grant (editor), *Hackh's Chemical Dictionary*, McGraw Hill, New York, 1969, p. 595.
Vogel, A., *Practical Organic Chemistry*, 2nd edition, Longmans, Green, New York, 1951, pp. 149-150.

*Primary Examiner*—Richard A. Schwartz
*Attorney, Agent, or Firm*—Steinberg & Raskin

[57] ABSTRACT

4(5)-Hydroxymethyl-5(4)-methylimidazole (MHI) is prepared by a process comprising the steps of:
  (a) reacting 4-methylimidazole (MI) with from 1.05 to 1.1 moles of formaldehyde or an equivalent amount of paraformaldehyde per mole of MI, in a concentrated aqueous NaCl solution in the presence of a catalytically effective amount of a strong inorganic base, at a temperature from about 20° to about 60° C.;
  (b) neutralizing the reaction mixture with concentrated aqueous hydrochloric acid to a pH of 8.5-8.9 to obtain a precipitate of MHI free base; and
  (c) separating the precipitate thus obtained from the aqueous solution and washing it with cold water or acetone.

The MHI free base thus obtained can further be converted to an acid addition salt thereof.

19 Claims, No Drawings

PREPARATION OF 4(5)-HYDROXYMETHYL-5(4)-METHYLIMIDAZOLE

FIELD OF THE INVENTION

The present invention relates to the manufacture of 4(5)-hydroxymethyl-5(4)-methylimidazole (hereinafter "MHI") which is an important intermediate in the synthesis of drugs, in particular the well-known H2-antagonist and anti-ulcer agent Cimetidine.

MHI exists in two tautomeric forms which are in equilibrium with each other and can be represented by the formulae:

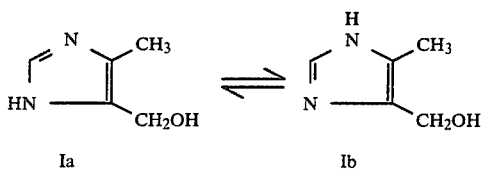

BACKGROUND OF THE INVENTION

It is well known in the art that the above mentioned syntheses of Cimetidine and related drugs require the use, as intermediate, of MHI of high purity (not less than 97% assay), because the presence of excessive amounts of impurities adversely affects the quality of the subsequent intermediates prepared from the MHI and of the Cimetidine end-product.

One of the main impurities present in commercial MHI or its hydrochloride salt is 2,5-di(hydroxymethyl)-4-methylimidazole (hereinafter "DMHI") which is formed as a byproduct in the hydroxymethylation of 4-methylimidazole (hereinafter "MI"). Other impurities are unchanged MI and imidazole which usually contaminates the MI starting material.

The object of the present invention is to provide an improved process for the manufacture of high quality MHI including only minimal amounts of the above mentioned impurities which process should have the further advantage of providing high yields of said product while requiring only comparatively simple and convenient work-up procedures.

PRIOR STATE OF THE ART

The early reports of Windaus (Ber. 42, 759 (1909), Ewins (J. Chem. Soc. 99, 2052 (1911)) and Erlenmeyer et al. (Helv. Chim. Acta 31, 38(1948)) describe the synthesis of MHI by reacting MI with aqueous formaldehyde under various conditions of high temperatures and pressures. However, all these methods provide only very low yields of MHI of poor quality so as to render them unsuitable for industrial use.

More recently, British Pat. No. 1,341,376, Belgian Pat. Nos. 832,660 and 944,830 and DURANT et al. (J. Med. Chem. 1976, 19(7), 925), reported the preparation of MHI by reduction of lower alkyl esters of 4-methylimidazole-5-carboxylic acid by means of, e.g. lithium aluminium hydride (LiAlH$_4$) or sodium in liquid ammonia. These processes are not feasible for industrial use, mainly owing to the high costs of the reducing agents employed, the costly and complicated equipment required and the cumbersome procedures which must be employed for purifying the crude products obtained.

German patent application Nos. 2,825,547 (1978) and 2,908,212 (1979) describe the preparation of the MHI.HCl acid addition salt by reacting MI with aqueous formaldehyde in the presence of concentrated HCl at elevated temperatures and pressures, for comparatively long periods of time. The products obtained by these procedures are of very inferior quality.

A further method for the preparation of the MHI.HCl acid addition salt in reasonable yields (51–67%) was disclosed in Israel Pat. No. 58130 (equivalent to British Pat. No. 2,029,414 and U.S. Pat. No. 4,275,216). In accordance with this method MI is reacted with paraformaldehyde in the presence of a strong base at temperatures of 30°–95° C., preferably 50°–80° C. However, this method involves a long and tedious work-up for the isolation of the MHI.HCl product and affords this product at comparatively low quality which does not conform with analytical specifications.

A still further process for the preparation of MHI in free base form or its hydrochloride salt was disclosed in European patent application No. 0,004,534 and the corresponding U.S. Pat. No. 4,189,591. This process consists in the reaction of MI with aqueous formaldehyde or paraformaldehyde (at a maximum excess of 0.5 mole) in a strongly alkaline aqueous medium (pH 11–13) at a temperature of 30°–40° C. This process too involves a long and cumbersome work-up for the isolation of the MHI free base or the HCl salt, usually including removal of the water by distillation in vacuo, which is a considerable drawback as far as industrial application is concerned. Furthermore, the process results in a low quality product which does not meet the analytical specifications with regard to assay and presence of impurities.

Summing up, it is observed that all the above known processes necessitate long and tedious work-up procedures, involving large amounts of solvents, a comparatively large number of operational steps, such as distillations, evaporations and/or prolonged heating at elevated temperatures and difficult lengthy filtrations. These drawbacks of the known processes are due primarily to the high water-solubility of MHI and its hydrochloride salt. Consequently, in some of these known processes isolation of the products is achieved by changing the aqueous reaction medium into an organic medium.

SUMMARY OF THE INVENTION

It has now surprisingly been found in accordance with the present invention that the solubility of the MHI free base in water, at a carefully controlled pH range of 8.5–8.9 (preferably 8.6–8.7), is considerably and selectively reduced to a very low percentage, if the aqueous reaction medium contains high concentrations of inorganic salts, preferably sodium chloride, whereas the main impurities, in particular DMHI, remain in the aqueous solution.

This unexpected finding enables the production of MHI by reaction of MI with formaldehyde in a concentrated aqueous NaCl solution in the presence of a catalytic amount of a strong inorganic base, followed by adjustment of the pH to the aforementioned range of 8.5–8.9, to obtain directly high yields (71–74%) of the desired MHI in free base form as a white precipitate of high purity.

The invention thus provides a process for the preparation of 4(5)-hydroxymethyl-5(4)methylimidazole (MHI) and acid addition salts thereof which comprises the steps of:

(a) reacting 4-methylimidazole (MI) with from 1.05 to 1.1 moles of formaldehyde or an equivalent amount of paraformaldehyde per mole of MI, in a concentrated aqueous NaCl solution in the presence of a catalytically effective amount of a strong inorganic base, at a temperature from about 20° to about 60° C.;

(b) neutralizing the reaction mixture with concentrated aqueous hydrochloric acid to a pH of 8.5–8.9 to obtain a precipitate of MHI free base;

(c) separating the precipitate thus obtained from the aqueous solution and washing it with cold water or acetone; and (d) if desired, converting the MHI free base thus obtained to an acid addition salt thereof, by known means.

In step (a) of the process of the invention paraformaldehyde is preferably used as the formaldehyde source, the reaction medium is preferably a saturated aqueous NaCl solution and the inorganic strong base is preferably caustic soda (NaOH). Suitable catalytic amounts of the strong base range from 0.15 to 0.30 equivalents per mole of the MI reactant. The reaction of step (a) is preferably conducted at a temperature from 30° to 40° C.

The white precipitate of MHI free base formed in step (b) of the process of the invention, is conveniently separated from the aqueous mother liquor by filtration or centrifugation. The filter cake has to be washed in order to free it from adhering aqueous NaCl. Ice-cold water is suitably used for washing and it was found that two such washes resulted in a pure MHI product of 97–99.9% assay. The product may then be dried at moderately elevated temperatures, e.g. 60° C.

As stated above, high yields (71–74%) of the MHI free base of 97–99.9% assay are obtained by the process of the invention. These yields can be increased by a further 10–15% by recycling the mother liquors of the reaction which contain the unreacted MI starting material.

The MHI free base obtained in accordance with the present invention, is of excellent quality, considerably superior to the hitherto available base or hydrochloride salt, and contains the usual impurities, namely DMHI, MI and imidazole at minimal levels of less than 0.5% each.

In the optional step (d) of the process of the invention, the MHI free base product may be converted, if desired, to an acid addition salt, most preferably the hydrochloride salt, by conventional procedures. Thus, the hydrochloride salt may be prepared by reacting a suspension of the MHI base in a suitable organic solvent (e.g. isopropanol) with gaseous HCl or with concentrated aqueous hydrochloric acid. The hydrochloride salt can thus be obtained in almost quantitative yields (93–95.5%) and at high purity (97–99% assay) with the same minimal contents of impurities as specified above for the MHI free base.

The invention will now be illustrated in more detail by the following non-limiting examples.

EXAMPLE 1

Preparation of MHI free base

A 3-necked, 1000 ml flask, equipped with a mechanical stirrer, reflux condenser and a thermometer, was charged with a solution of 72 g of NaCl in 292 ml of water. 200 g of 4-methyl-imidazole were added followed by 14 g of NaOH, while the temperature was maintained at 30°–35° C. The resulting emulsion was cooled and 80 g of paraformaldehyde were gradually added while keeping the temperature at 35°–40° C. In the course of the addition of paraformaldehyde the initial emulsion turned into an almost clear solution. The reaction mixture was cooled to 30° C. and stirred at that temperature for 43 hours. The thick, yet stirrable mixture, was neutralized with concentrated aqueous HCl (35.8 ml) to a pH of 8.6–8.7, while cooling and maintaining the temperature at 25–30° C. The pH was measured by means of an electrode immersed in the reactor. Alternatively, a sample can be taken from the reaction mixture, and the pH thereof measured as such (without dilution). The reaction mixture was further stirred at room temperature for about half an hour, cooled to 8° C., kept at this temperature for about 3 hours, and filtered off. The filter cake was washed with three portions of acetone (100 ml each) and dried at 60° C. Yield: 192 g (73%) of white powder, m.p.: 135.8–°136.2° C. Analysis:

| Ash | 0.3% |
|---|---|
| Assay | 99.1% |

DMHI, MI and imidazole - each <0.5% (by TLC and HPLC analyses)

EXAMPLE 2

MHI.HCl from the free base

Procedure A (using gaseous HCl)

30 g of MHI free base were suspended in 120 ml of isopropanol and 10.2 g of HCl gas were bubbled into the suspension under stirring. A temperature rise to 60° C. was observed. The mixture was then cooled to 8° C. and stirred at that temperature for 4 hours. The resulting precipitate was filtered off and dried. Yield: 37.4 g (0.253 mol, 94%), m.p.: 234°–236° C.

Procedure B (using aqueous HCl)

20 g of MHI free base were added to 22 g of concentrated aqueous HCl and the resulting solution stirred at room temperature for 15 minutes. 80 ml of isopropanol were added followed by 25 ml of cyclohexane. Water was removed from the reaction mixture by azeotropic distillation (26 ml of isopropanol-water azeotrope were collected). The distillation was continued until the vapour temperature reached 68° C. The residual mixture was cooled to 8° C. and stirred at this temperature for 4 hours. The resulting precipitate was filtered off and dried.

Yield: 24.6 g (0.166 mol, 93%), m.p.: 234°–236° C. Analysis:

| Ash | 0.2% |
|---|---|
| Assay | 98% |

DMHI, MI and imidazole - each <0.5% (by TLC and HPLC analyses).

EXAMPLE 3

Manufacturing Scale Preparation of MHI

A Pfaudler reactor of 3000 l capacity equipped with a mechanical stirrer, reflux condenser and thermometer, was charged with 1200 l of water and 288 kg of technical NaCl and the mixture was stirred at room temperature until the salt dissolved. Thereafter, 800 kg of technical 4-methylimidazole was added which resulted in a yellow emulsion. The mixture was held at a temperature of 25° to 30° C. and 56 kg of caustic soda flakes were slowly added while keeping the temperature at about 35° C. After stirring and cooling to 25° C., 320 kg of technical paraformaldehyde were added while keeping the temperature at 30° to 35° C. The reaction mixture was then cooled to 30° C. and kept at that temperature while stirring for about 40 hours. In a second run, the reaction mixture was stirred at 35° C. for 26 hours which, however, led to a slight decrease in yield (in the order of 3 to 4%).

After completion of the reaction, the mixture was carefully neutralized with about 140 kg of technical concentrated aqueous HCl (32%) while maintaining the temperature at 30° C., until the pH of the mixture dropped to 8.6-8.9. The acidification is only slightly exothermic. The reaction mixture was then cooled to 10° C. and kept at this temperature while stirring for 3 hours.

The precipitate formed was filtered off and the resulting filter cake was washed well with two 300 l portions of ice cold (2° C.) water, with an interval of half an hour between the two washes. The product was then dried in an oven at a maximum temperature of 70° C.

Yield: 767 kg (71%) of white powder, m.p.: 136°-137° C.

Analysis

| Loss on Drying | nil. |
| Ash | 0.17% |
| Assay | 98.8% |

DMHI, MI and imidazole - each <0.5% (by TLC and HPLC analyses).

We claim:

1. A process for the preparation of a 4(5)-hydroxymethyl5(4)-methylimidazole (MHI) of the tautomeric formulae

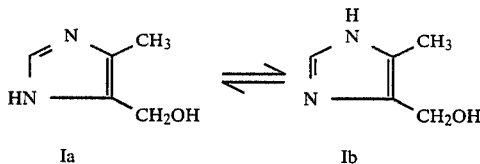

Ia          Ib which comprises the steps of:
(a) reacting 4-methylimidazole (MI) with from 1.05 to 1.1 moles of formaldehyde or an equivalent amount of paraformaldehyde per mole of MI, in a concentrated aqueous NaCl solution in the presence of a catalytically effective amount of a strong inorganic base, at a temperature from about 20° to about 60° C.;

(b) neutralizing the reaction mixture with concentrated aqueous hydrochloric acid to a pH of 8.5-8.9 to obtain a precipitate of MHI free base; and (c) separating the precipitate thus obtained from the aqueous solution and washing it with cold water or acetone;

2. A process according to claim 1 wherein paraformaldehyde is used in step (a) as the formaldehyde source.

3. A process according to claim 1 wherein the reaction in step (a) is conducted in a saturated aqueous NaCl solution.

4. A process according to claim 1 wherein the reaction in step (a) is conducted at a temperature from about 30° to about 40° C.

5. A process according to claim 1 wherein said strong inorganic base used in step (a) is caustic soda (NaOH).

6. A process according to claim 1 wherein from 0.15 to 0.30 equivalents of said strong inorganic base are used per each mole of MI.

7. A process according to claim 1 wherein in step (b) the reaction mixture is neutralized to a pH of 8.6-8.7.

8. A process according to claim 1 wherein the separation of the precipitate in step (c) is effected by filtration.

9. A process according to claim 1 wherein the precipitate in step (c) is washed with ice-cold water.

10. A process according to claim 1 wherein the aqueous solution (mother liquor) obtained in step (c) is recycled for use in step (a) of a subsequent batch.

11. The process of claim 1, comprising the additional step of (d) converting the MHI free base thus-obtained to an acid addition salt thereof.

12. The process of claim 1, wherein separation of the precipitate in step (c) is effected by centrifugation.

13. The process of claim 9, wherein the precipitate is washed a second time with the ice-cold water in step (c).

14. The process of claim 1, wherein the thus-obtained MHI includes minimal levels of DMHI, MI, and imidazole impurities of less than 0.5% each.

15. The process of claim 11, wherein in step (d), the MHI free base is converted to a hydrochloride salt by reacting a suspension of the MHI base in organic solvent with gaseous or concentrated aqueous HCl.

16. The process of claim 15, wherein the organic solvent used in step (d) is isopropanol.

17. The process of claim 4, wherein, in step (a)
(1) the MI, inorganic base and concentrated NaCl solution, are first mixed at a temperature of 30°-35° C. to form an emulsion, and
(2) the paraformaldehyde was then added to the emulsion at a temperature of 35°-40° C.

18. The process of claim 17, wherein, in step (b), the temperature is maintained at 25°-30° C. during the neutralization.

19. The process of claim 2, wherein, in step (a)
(1) the MI, and concentrated NaCl solution are first mixed at a temperature of 25°-30° C.,
(2) caustic was then added while the temperature was maintained at about 35° C., and
(3) the paraformaldehyde was then added at a temperature of 30°-35° C.

* * * * *